United States Patent
Abedini

(10) Patent No.: US 11,378,563 B2
(45) Date of Patent: Jul. 5, 2022

(54) METHOD FOR QUANTIFYING FUGITIVE METHANE EMISSIONS RATE USING SURFACE METHANE CONCENTRATION

(71) Applicant: Ali Reza Abedini, North Vancouver (CA)

(72) Inventor: Ali Reza Abedini, North Vancouver (CA)

( * ) Notice: Subject to any disclaimer, the term of this patent is extended or adjusted under 35 U.S.C. 154(b) by 81 days.

(21) Appl. No.: 16/888,676

(22) Filed: May 30, 2020

(65) Prior Publication Data

US 2020/0371079 A1 Nov. 26, 2020

(51) Int. Cl.
*G01N 33/00* (2006.01)
*G01N 27/626* (2021.01)

(52) U.S. Cl.
CPC ....... *G01N 33/0062* (2013.01); *G01N 27/626* (2013.01)

(58) Field of Classification Search
CPC ........... G01N 33/0062; G01N 33/0006; G01N 33/0004; G01N 27/626
See application file for complete search history.

(56) References Cited

U.S. PATENT DOCUMENTS

| | | | |
|---|---|---|---|
| 2012/0191349 A1* | 7/2012 | Lenz | G01N 33/0075 702/2 |
| 2017/0218731 A1* | 8/2017 | Campanella | E21B 43/00 |
| 2021/0017926 A1* | 1/2021 | Alkadi | G07C 5/006 |
| 2021/0255158 A1* | 8/2021 | Smith | H04L 5/0044 |

OTHER PUBLICATIONS

Park, Jin-Kyu et al., "Estimation of Methane Emission Flux at Landfill Surface using Laser Methane Detectr: Influence of Gauge Pressure", Aug. 2016, SAGE Publications, Waste Management & Research, vol. 34, Edition 8, pp. 784-792.*

* cited by examiner

*Primary Examiner* — Manuel L Barbee

(57) ABSTRACT

A method was invented to convert methane concentration at the surfaces emitting fugitive methane into methane emission rate. This method requires surface scan of methane concentration using handled devices such as flame ionization detector (FID) to measure the fugitive methane near-surface concentration based on which, the methane emission rate can be calculated using a correlation expressed in a mathematical form.

1 Claim, 4 Drawing Sheets

METHOD FOR QUANTIFYING FUGITIVE METHANE EMISSIONS RATE USING SURFACE METHANE CONCENTRATION

BACKGROUND OF INVENTION

1. Field of Invention

This invention relates generally to methods for measurement and estimation of fugitive methane emission rates from the surface of a landfill or any other source of fugitive methane emission specifically using concentration of fugitive methane near the surface of the emitting source.

2. Description of the Related Art

Landfill gas (LFG) is a by-product of natural decomposition of organic materials in landfills that can create unsafe air quality, health issues, unpleasant odours, and contribute to global climate change. LFG predominantly consists of methane ($CH_4$) and carbon dioxide ($CO_2$); both being potent greenhouse gases (GHG). While $CO_2$ produced in the waste sector (e.g. municipal landfills, wastewater treatment plants, and burning of non-fossil fuel waste) is not accounted for as a GHG due to its biogenic origin, the fugitive emission of $CH_4$ from landfills is of significant concern (IPCC, 2006) in terms of global warming potential (GWP). Methane is a naturally occurring GHG with a GWP 28 to 34 times greater than carbon dioxide over a 100-year timeframe (IPCC, 2013). In Canada, about 3% of the 2010 national GHG emissions were reported to be from the waste sector, of which about 91% was attributed to fugitive methane emissions from landfills (Environment Canada, 2012).

Methane is an important GHG with a much shorter atmospheric lifetime, approximately 10 years, in comparison with other greenhouse gases (Bogner and Matthews, 2003). Accordingly, changes made to $CH_4$ emission sources can affect the atmospheric concentrations on relatively shorter timescales.

Attention to methane emissions from landfills has grown significantly due to the fact that emission reduction from landfills is amongst the most feasible and cost-effective measures to reduce greenhouse gas emissions (Kormi et al, 2018). However, quantifying landfill fugitive methane emissions is challenging due to the high temporal variability and spatial heterogeneity.

Thus, development of reliable and cost-effective methods for measurements of landfill methane emissions is critically important.

Various methods have been attempted by scientists and practitioners over the past few decades. The most widely method seemingly more favorable for the purpose of regulatory compliance assessment is the use of flux chamber which directly measures methane emission flux from the surface of landfills. In addition to chamber methods, other methods including but not limited to eddy covariance and co-advected prow tracer plume measurements and methods relying on remote sensing and plume mapping have been used (Gardiner et al., 2017; Delre et al., 2018; Kormi et al., 2017; Goldsmith et al., 2012; Gollapalli et al., 2018; Monster et al., 2014: Innocenti et al., 2017; Delkash et al., 2016; Allen et al., 2018). Chamber-based measurements are relatively easy to conduct as emissions can be estimated from the rate of change of $CH_4$ concentration in a chamber, the footprint area of the chamber and volume of the chamber. However, the chamber method suffers practical drawback due to the typically heterogeneous nature of the landfill resulting in high spatial variability of emissions (Riddick et al., 2018).

Eddy covariance (EC) methods have also been studied for methane emission estimation from landfills over longer periods of time, Xu et al. (2014). Eddy covariance which calculates a gas flux from the covariance between vertical wind speed and gas concentration at a high sampling rate has the main advantages of providing mean flux estimates over a larger area and being automated. The drawbacks however are that the emission in the fetch needs to be homogeneous and that the measurement needs to be carried out on a topographically flat surface to obtain meaningful results (Riddick et al., 2018).

Using acetylene as the tracer gas is the current state of the art tracer gas dispersion measurements for determining methane emissions from landfills. Measurements of the tracer gas and methane concentrations are made downwind of the source (Mønster et al. 2015). The tracer gas dispersion technique relies on the assumption that full mixing between the tracer and landfill plume has occurred at the point of monitoring (Rees-White et al., 2018). A key logistical limitation of the tracer release method is that it requires a mobile measurement team to coordinate with the person releasing the gas and then traverse an accessible road perpendicular to the landfill plume in the time it takes for the plume to travel from the release site. Furthermore, it should be ensured that the tracer gas is well mixed with the landfill methane as insufficiently mixed plumes can invalidate the co-advection assumption, result in large uncertainties in the emission estimate (Riddick et al., 2018).

Additionally, the relationship between the emission rate and the gas concentration at a given location is dependent on the meteorological conditions and local topography, preventing accurate quantification of the emission rate.

Remote sensing techniques represent a more integrated approach for quantification of methane flux. These techniques have gained popularity in recent years. One of these techniques is the Radial Plume Mapping (RPM) methodology recognized by the US-EPA as "other test method 10 (OTM-10)" since July 2006 (USEPA, 2006). This technique uses optical remote sensing (ORS) instrumentation to characterize gas emissions from non-point sources. Some of these ORS instruments include; (i) Open-Path Fourier Transform Infrared (OP-FTIR) spectroscopy. (ii) Ultraviolet Differential Absorption Spectroscopy (UV-DOAS), and (iii) Open-Path Tunable Diode Laser Absorption Spectroscopy (OP-TDLAS) (USEPA, 2007).

The RPM techniques carry many advantages over the "close range measurement" methodologies, such as the flux chamber technique. However, the relatively high cost of the RPM method, as well as the uncertainties associated with the possible effect of the methane plume buoyancy on the results, made the flux chamber methodology a more suitable option for the present invention.

Prior to the applicant's invention, no methods were known to utilize a relationship between surface concentration of fugitive methane from a landfill surface and the emission rate of methane typically or as an accepted standard method measured using flux chamber. More specifically, prior to this invention, a correlation between the concentration of fugitive surface concentration of methane and methane flux or emission rate that can be generalized to other typically similar landfills, only through adjustment of barometric pressure has not been developed.

Several embodiments of the present invention relate to a methodology using which fugitive methane emission can be characterized and quantified for further applications such as reporting methane emissions for regulatory purposes, evaluating performance of landfill bio-covers and identifying hotspots in terms of methane emission.

BRIEF SUMMARY OF THE INVENTION

In accordance with several embodiments of the invention, a method wherein the fugitive methane emission rate is calculated based on surface concentration of fugitive methane measured using surface scanning.

In one embodiment of the method in accordance with this invention, this method is based upon a strong correlation developed between landfill surface methane concentration (SMC, part per million volume (ppmv) $CH_4$) and methane emission rate (MER, g $CH_4/m^2/d$).

In one embodiment, landfill is a confined or semi-confined space wherein different types of waste materials are disposed of following a standard procedure prescribed by local, regional, national or international authorities and regulatory bodies.

In a preferred embodiment, landfill as defined above, receives municipal solid waste that includes organic materials which can decompose and generate methane.

In one embodiment, the landfill is equipped with a cover or a cap through which fugitive methane generated as a result of anaerobic decomposition of organic material inside the landfill is emitted to the atmosphere.

In one embodiment, the landfill is equipped with landfill gas collection system through which all gases including methane generated within the body of landfill excluding the portion emitted fugitively into the atmosphere are collected for further processing.

In one embodiment, the cap over the landfill will be made of layers of different earthen or synthetic materials aimed at reducing fugitive methane emission.

In preferred embodiment, quantification of fugitive emission is critically important to quantify the landfill contribution to overall greenhouse gas emission and climate change.

In one embodiment, the landfill is divided into several zones. In preferred embodiment, the zones are selected based on geometry, type of cover, type or status of vegetation including but not limited to healthy and stressed, other visual observation, expected emission levels and pre-sampling results if such results are available.

In preferred embodiment, measurement of surface methane concentration (SMC) is completed through a modified version of an existing protocol for qualitative assessment of emissions from municipal landfills established by the United States Environmental Protection Agency (US EPA) (Title 40 CFR Pat 60, Standards of Performance for Municipal Solid Waste Landfills).

In preferred embodiment, SMC values are adjusted accounting for effects of barometric pressure rate of change during sampling campaign.

In one embodiment, adjusted SMC data are integrated for each measurement zone to calculate an average adjusted SMC for each zone.

In preferred embodiment, the adjusted average SMC in each zone is correlated with the average methane flux measured within each zone based on standard protocols available including but not limited to the Flux Chamber method.

In preferred embodiment, the resulting correlation in form of an equation can be used under a variety of methane emitting surfaces such as landfills, to calculate methane emission rate solely based on surface methane concentration requiring none, minimum or limited number of emission rate measurements through methods such as flux chamber.

In preferred embodiment, the method presented in this invention can be used in a variety of landfills where methane emission rate is to be reported.

The preferred embodiment relies solely on significantly cost effective and less time-consuming measurement of surface methane concentration as an advantage to the existing methods such as using flux chambers for methane emission rate measurement.

The one embodiment, the equation can be recalibrated and/or validated for a new methane emitting site or a methane emitting site with significantly different surficial features through additional yet limited number of flux chamber measurement data points.

DETAILED DESCRIPTION OF THE INVENTION

A unique approach was developed under this research allowing for quantification of the fugitive methane emissions rate (MER) from the entirety of a given landfill surface area at a considerably lower cost in comparison with the conventional methods. The core of the proposed method is to use measured surface methane concentration (SMC) data obtained through surface scan by handheld devices such as a portable flame ionization detector (FID).

The correlation between SMC data and MER values was developed based on representative emission rate values measured using flux chamber technique and adjustments made in terms of barometric pressure fluctuations during the fieldwork. The resulting equation can be used to simply predict the methane flux through the surface of any given landfill (active, cover soil, or biocover), using SMC data which are obtained through a less costly method.

Figure 4:
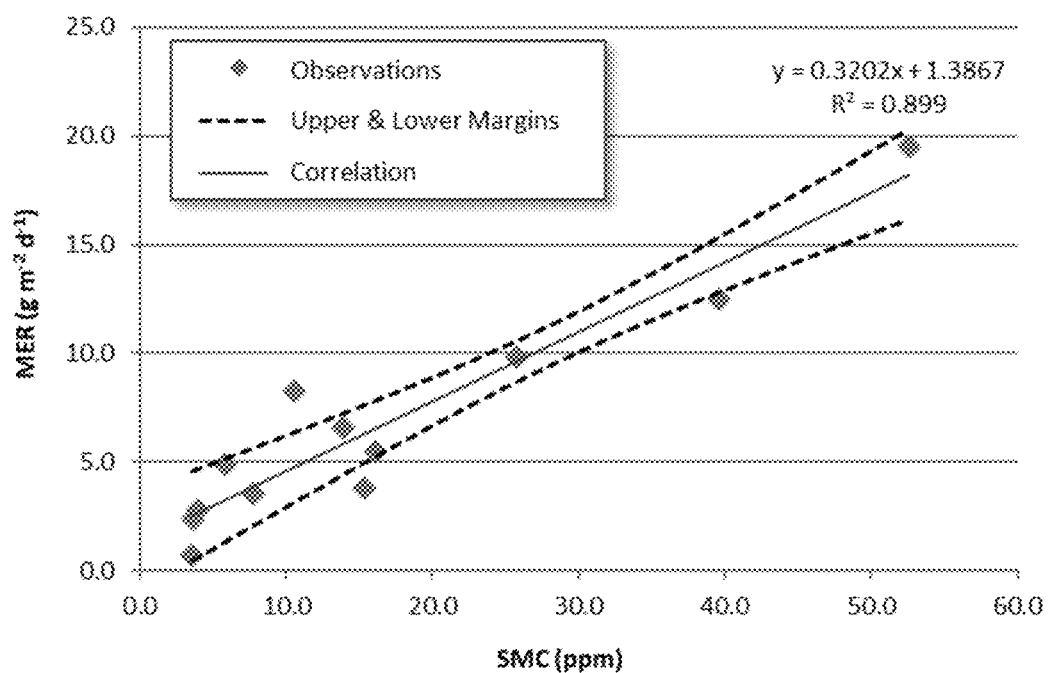

In this invention, this method may be accomplished through the following steps:
(i) Area of interest or the project boundary such as landfill footprint is divided into several zones denoted as $Z_i$, based on one or more of the following attributes of a given site; landfill or otherwise:
  a. The geometry of the site,
  b. Type of cover including but not limited to earthen covers, geosynthetics, biocover and a combination of different types of covers
  c. Type of vegetation,
  d. Status of vegetation in terms of density, health and level of stress
  e. Other visual observations,
  f. Expected emission levels in terms of concentration or rate based on any previous field measurement records
  g. Expected or anticipated emission levels in terms of concentration or rate based on the results of previous emission rate or concentration modeling
(ii) Measurement of SMC is completed through any of existing or future protocols and standards for qualitative assessment of emissions from municipal landfills established by regulatory or otherwise organizations such as the US EPA, Title 40 CFR Pat 60, Standards of Performance for Municipal Solid Waste Landfills, (iii) SMC values are adjusted to $SMC_a$ accounting for effects of barometric pressure rate of change during sampling campaign, (iv) $SMC_a$ data are integrated for each measurement zone to calculate an average $SMC_a$ for each zone denoted as $SMC_{a-i}$, and (v) $SMC_{a-i}$ values in form of data points or measurements for each zone is correlated linearly to quantitative measurement data points of $MER_{a-i}$ which is the Average Methane Emission Rate for Zone $Z_i$ (vi) The correlation as shown in Equation 1, and in FIG. 4, results in a Correlation Factor $C_f$.

$$MER_{a-i} = SMC_{a-i} \times C_f \pm \Delta SMC_{a-i} \quad \text{Equation 1}$$

Where:
$MER_{a-i}$=average methane emission rate for zone $Z_i$ in g $CH_4/m^2/d$
$SMC_{a-i}$=average surface methane concentration for zone $Z_i$ in ppmv $CH_4$
$C_f$=Correlation factor For every calculated numeric value of the $SMC_a$ for each zone, a corresponding $MER_a$ can be calculated using Equation 1 and the line shown in FIG. 4 denoted as Correlation.

Values for the correlation factor and variation are developed under this work and provided through the correlation and the total methane emission from the project boundary abbreviated as E r can be then calculated as:

$$E_T = \Sigma_{i=1}^{n}(A_i \times MER_{a-i} \times 3.65 \times 10^{-4}) \quad \text{Equation 2}$$

Where:
$E_T$=total annual methane emission from the project boundary in tonnes/year
$A_i$=Footprint Area of zone $Z_i$ in $m^2$
$MER_{a-i}$=average methane emission rate for zone $Z_i$ calculated from Equation 1 in g $CH_4/m^2/d$
$3.65 \times 10^{-4}$=unit conversion multiplier Note: The default correlation factor $C_f$ is developed by completing a quantitative field measurement of MER using the US EPA flux chamber methodology for various zones with different emission levels, qualitative assessment of SMC for the same areas, and plotting the SMC data against the MER values. Similar exercise can be repeated, when possible and desired, to calculate a site-specific value for $C_f$.

A) Zoning: Zoning of a site is necessary only if different areas of the site are expected to have significantly different methane emission rates. This is done prior to completing the field measurements. The area of interest is divided into different zones based on expected levels of methane emission rates such as landfill crest, side slopes, type of cover, type of vegetation, etc. While the end results in form of the estimated total methane emission from the site will remain the same, zoning of the site will help identifying the areas with higher emission rates.

Figure 1:
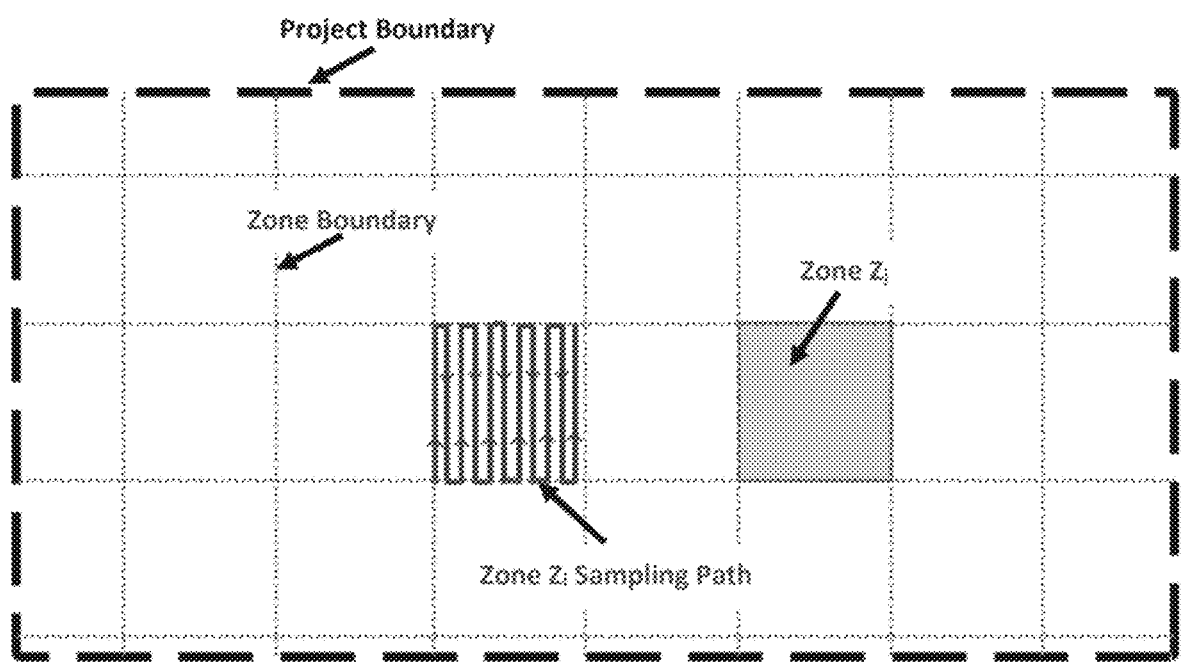
FIG. 1. Sampling path within a zone
FIG. 2. BP change rate and MER multiplier correlation
FIG. 3. $SMC_a$ and $MER_a$ for 12 zones
FIG. 4. SMC and MER correlation

B) Field measurement abbreviated as SMC: Surface methane concentration of each zone is measured by continuous and instantaneous sampling of air using a portable device with minimum detection limit of 0.0001% methane or 1 part per million or ppm. One of the devices that can be used to measure SMC with this accuracy is portable Flame Ionization Detector denoted as FID to measure the concentration of total organic compounds measured as methane at the landfill surface. SMC measurement is completed following the protocols similar to US EPA protocol for qualitative surface methane emission monitoring under Title 40 CFR Part 60, Subpart WWW. Method includes instantaneous sampling of air at 2.5 to 10 cm above landfill surface and on paths of approximately 30 m. Reducing the distance between the measurement paths which is recommended to be 10 m or less, will increase number of samples and accuracy of the results. The SMC measurement field work can be completed only when the landfill cover soil, biocover, or other form of covers is not saturated, and wind speed is less than 16 km/hr equal to about 4.5 m/sec. The SMC readings are recorded at minimum every 5 to 10 seconds at sampling points approximately every 1 to 2 m along the sampling route or path. These readings are separately collected for each zone along with GPS records, time of sampling, climate conditions, ambient temperature and barometric pressure. FIG. 1 shows an example of how a site boundary is divided into different zones and how sampling path should be in an example zone.

C) Other field readings and field data adjustments:
Variations in the weather conditions, and in particular the barometric pressure abbreviated as BP, have an impact on rate of methane fugitive emissions from landfill's surface. Higher emission rates at landfills are reported to occur at lower ambient pressures. In general, variations in atmospheric pressure happen due to several factors including;
Auto oscillation of air which is reported to have an insignificant effect,
Daily warming and cooling of air caused by solarization causing diurnal variations, and
Passage of atmospheric pressure lows and highs leading to long term variations.

Figure 2:
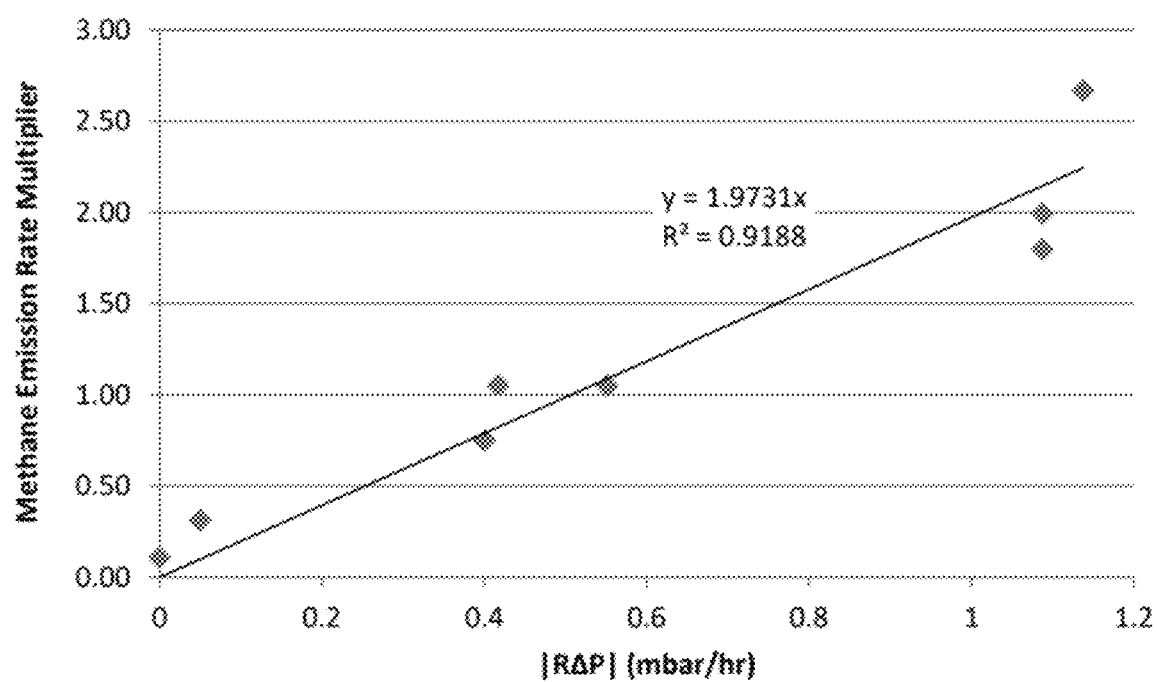

Therefore, short term daily and long term seasonal variations in atmospheric pressure should be considered when conducting methane fugitive emission measurements at a landfill site. The present methodology includes development of an equation for adjusting the calculated MER values for effect of barometric pressure fluctuations at time of sampling. The true value of MER at the landfill could be measured when the atmospheric pressure remained constant, causing an equilibrium condition between landfill and the surrounding environment. The following equation was developed through finding a good correlation between change in MER values and rate of change in barometric pressure as shown in FIG. 2.

Therefore, the MER values should be adjusted to the true values presented as $MER_a$, based on the recorded $\Delta P/t$ at the time of sampling relative to the equalized condition meaning that $\Delta P/t$ equals zero.

$$MER_a = MER \times (1 + 1.9731 \times |\Delta P/t|)^{(\Delta P/t/|\Delta P/t|)} \quad \text{Equation 3}$$

Where:
$\Delta P/t$=change in barometric pressure over time during sampling
$\Delta P/t/|\Delta P/t|$ would be equal to $-1$ or $+1$, represent the sign of the $\Delta P/t$. This adjustment for effect of BP shall be made once on either measured SMC data or calculated MER at the end as suggest in Equation 3. If field data is intended to be adjusted before calculation of MER. Equation 4 below can be used to find adjusted SMC, based on which true value of MER can be calculated.

$$SMC_a = SMC \times (1 + 1.9731 \times |\Delta P/t|)^{(\Delta P/t/|\Delta P/t|)} \quad \text{Equation 4}$$

D) Data compilation and analyses:
This invention is based on the correlation that was found between SMC and MER. This correlation, illustrated in FIGS. 3 and 4 below, was developed through extensive field measurement on 12-hectare area consisting of 12 different measurement zones.

Figure 3:
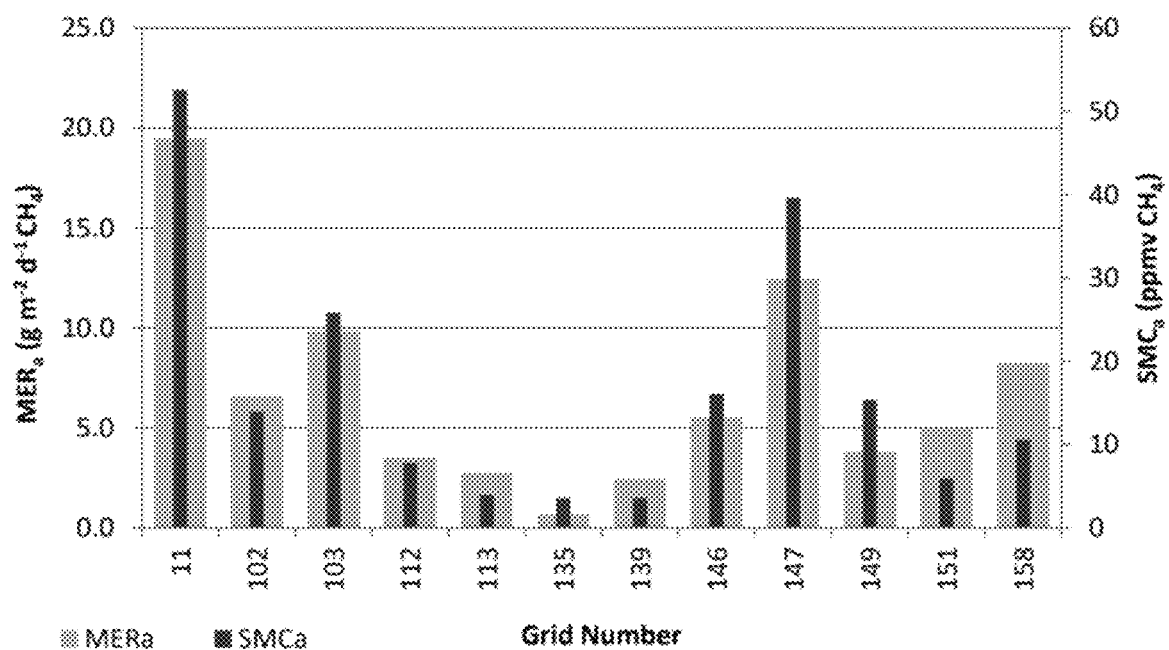

As shown in FIG. 3, plotting the $SMC_a$ data against the MER values showed a reasonable correlation between these two values.

Based on this correlation:

$$MER = SMC \times (0.32 \pm 0.034) + (1.39 \pm 0.755) \qquad \text{Equation 5}$$

Where:

MER=methane emission rate in g $CH_4$ $m^{-2}$ $d^{-1}$

SMC=surface methane concentration in ppmv $CH_4$

The development of this invention can be practically very important in the LFG management industry, saving time and money when full scale fugitive methane emission measurements are required. Another very important application of this methodology is performance review and/or quantification of methane emission from surfaces with very low methane emissions such as bio-cover systems, bio-filters, and bio-window systems.

Main objective of these systems is to minimize methane emission to the atmosphere, making it almost impossible to use conventional methods, such as flux chamber technique, for quantification of the remaining methane emission through these systems.

REFERENCES CITED

US Patents

U.S. Pat. No. 4,204,121—Cylindrical Method of Quantifying Fugitive Emission Rates from Pollution Sources U.S. Pat. No. 5,355,739—Apparatus for Measuring Gas Emission Rate from Soil U.S. Pat. No. 5,563,335—High Flow Rate Sampler for Primary Examiner-Michael J. Brock Measuring Emissions at Process Attorney. Agent, Or Firm-Hill, Steadman & Simpson Components U.S. Pat. No. 5,717,130—Method and Apparatus for Determining Emission Measurement Accuracy U.S. Pat. No. 6,611,760B2—Method and System for Estimating Gas Production by a Landfill or Other Subsurface Source U.S. Pat. No. 6,864,983B2—Method for Measuring of Gaseous Emissions and/or Flux US6999883B1—Landfill Gas Extraction Constant Flow Control Method and Device U.S. Pat. No. 7,748,253B2—Vent and Soil Flux Measurement System U.S. Pat. No. 7,856,899B2—Vent and Soil Flux Measurement System U.S. Pat. No. 8,010,300B1—Determination of Gas Flux Using Airborne Dial LIDAR U.S. Pat. No. 8,121,798B2—Gas Flux Determination Using Airborne Dal Lidar and Airborne Wind Measurement U.S. Pat. No. 8,714,034B2—Gas Flux Measurement Using Traps U.S. Pat. No. 8,781,755B2—Fugitive Emission Flux Measurement U.S. Pat. No. 8,950,251B2—Tracer Method to Estimate Rates of Methane Generation Through Augmentation or Biostimulation of the Sub-Surface U.S. Pat. No. 9,164,081B2—Method and Device for Determining Greenhouse Gas, In Particular Methane, Emitted By A Ruminant, In Particular a dairy Animal U.S. Pat. No. 9,435,782B2—Landfill Gas Surface Monitor and Methods U.S. Pat. No. 9,759,597B2—Methods for Calibration a Fugitive Emission Rate Measurement US2001/0034576A1—Portable On-Board Mass Emissions Measuring System US2008/0195329A1—Method for Detecting and Monitoring Emissions US2009/0136298A1—Collection of Landfill Gas at Variable Rates to Match Temporal Needs for Energy Generation US2010/0091267A1—Fugitive Emission Flux Measurement US2012/0290221A1—System and Method for Measuring GHG Emissions Associated To Bioproduct Industry US2012/0312530A 1—In-Situ Detection and Analysis of Methane in Coal Bed Methane Formations with Spectrometers Foreign Patent Documents WO 2010/004404 A1—On Line Sampling Device and Method to Analyze Volatile Compounds Emissions CA2476902C—Innovative gas monitoring with spatial and temporal analysis CN1203364A—Method for determining discharging quantity of gas from farmland greenhouse CN102331484A—Method for measuring discharged quantities of greenhouse gases of flowing water body CN203224388U—Static box for measuring animal waste greenhouse gas emission rate EP 2 647 991 B1—Methods and apparatus for measuring gas flux EP 2 770 820 B1—Method And Device For Determining Greenhouse Gas Emission From A Ruminant

OTHER PUBLICATIONS

Allen G., Hollingsworth P., Kabbabe K., PittJ. R., Mead M. I., Illingworth S., Roberts G., Bourn M., Shallcross D. E. and Percival C. J., 2018, The development and trial of an unmanned aerial system for the measurement of methane flux from landfill and greenhouse gas emission hotspots, Waste Management, In Press.

Bogner J. and Matthews E., 2003, Global methane emissions from landfills: New methodology and annual estimates 1980-1996, Global Biogeochemical Cycles 17(2): 1065.

Delkash M., Zhou B. and Singh R., 2016, Measuring landfill methane emissions using satellite and ground data, Remote Sensing Applications: Society and Environment 4, 18-29.

Delre A., Mønster J., Samuelsson J., Fredenslund A. M. and Scheutz C., 2018, Emission quantification using the tracer gas dispersion method: The influence of instrument. tracer gas species and source simulation, Science of the Total Environment, 634, 59-66.

Environment Canada, 2012, "1990-2010 National Inventory Report: Greenhouse Gas Sources and Sinks in Canada." The Canadian Government's Submission to the UN Framework Convention on Climate Change. 1910-7064.

Gardiner T., Helmore J., Innocenti F. I and Robinson R., 2017, Field Validation of Remote Sensing Methane Emission Measurements, Remote Sensing, 9, 956: doi: 10.3390/rs9090956.

Gebert J. and Groengroeft A., 2006, Passive landfill gas emission—Influence of atmospheric pressure and implications for the operation of methane-oxidising biofilters, Waste Management 26(3): 245-251.

Goldsmith Jr. D. C., Chanton J., Abichou T., Swan N., Green R. and Hater G., 2012, Methane emissions from 20 landfills across the United States using vertical radial plume mapping, Journal of the Air & Waste Management Association, 62:2, 183-197, DOI: 10.1080/10473289.2011.639480.

Gollapalli M and Harsha Kota S., 2018, Methane emissions from a landfill in north-east India: Performance of various landfill gas emission models*, Environmental Pollution 234, 174e180.

Innocenti F., Robinson R., Gardiner T., Finlayson A. and Connor A., 2017, Differential Absorption Lidar (DIAL) Measurements of Landfill Methane Emissions, Remote Sensing, 9, 953; doi:10.3390/rs9090953.

IPCC, 2006, "2006 IPCC Guidelines for National Greenhouse Gas Inventories, Volume 5: Waste. Prepared by the National Greenhouse Gas Inventories Programme, Eggleston H. S., Buendia L., Miwa K., Ngara T. and Tanabe K. (eds)." http://www.ipccnggip.iges.or.jp/public/2006gl/vol5.htm.

IPCC, 2013, "Summary for Policymakers. In: Climate Change 2013: The Physical Science Basis. Contribution of Working Group I to the Fifth Assessment Report of the Intergovernmental Panel on Climate Change." Cambridge University Press, Cambridge. United Kingdom and New York, N.Y., USA.

Klenbusch M. R., 1986, "USEPA—Measurement of gaseous emission rates from land surfaces using an emission isolation flux chamber: user's guide." http://nepis.epagov/Exe/ZvPURL.cgi?Dockey=930013RX.TXT (EPA/600/8-86/008): February, 1986.

Kormi T., Bel Hadj Ali N., Abichou T. and Green R., 2017, Estimation of landfill methane emissions using stochastic search methods, Atmospheric Pollution Research, 8, 97e605.

Kormi T., Mhadhebi S., Bel Hadj Ali N., Abichou T. and Green R., 2018, Estimation of fugitive landfill methane emissions using surface emission monitoring and Genetic Algorithms optimization, Waste Management, 72, 313-328.

Mønster J. G., Samuelsson J., Kjeldsen P., Rella C. W. and Scheutz C., 2014, Quantifying methane emission from fugitive sources by combining tracer release and downwind measurements—A sensitivity analysis based on multiple field surveys. Waste Management 34, 1416-1428.

Mønster J., Samuelsson J., Kjeldsen P. and Scheutz C., 2015, Quantification of methane emissions from 15 Danish landfills using the mobile tracer dispersion method, Waste Management, 35, 177-186.

Poulsen T. G., Christophersen M., Moldrup P. and Kjeldsen P., 2003, Relating landfill gas emissions to atmospheric pressure using numerical modelling and state-space analysis, Waste Management and Research 21: 356-366.

Prosser R. W., 1985, The effect of atmospheric pressure on the availability of gas from landfill. Anaheim, Calif. 92807, GC Environmental, Inc.

Rees-White T. C., Mønster J., Beaven R. P. and Scheutz C., 2018, Measuring methane emissions from a UK landfill using the tracer dispersion method and the influence of operational and environmental factors, Waste Management, In Press.

Riddick S. N., Hancock B. R., Robinson A. D., Connors S., Davies S., Allen G., Pitt J. and Harris N. R. P., 2018, Development of a low-maintenance measurement approach to continuously estimate methane emissions: A case study, Waste Management, 73, 210-219.

Scharff H., D. M. M. v. Rijn, Hensen A., Oonk J., A. de Visscher, Flechard C., Vroon R. and Boeckx P., 2003, A comparison of measurement methods to determine landfill methane emissions, NV Afvalzorg, Haarlem, The Netherlands.

SHA, 2000, "Sperling Hansen Associates, City of Vancouver Landfill Design and Operations Plan." (SHA-PRJ99026): January, 2000.

USEPA, 1999, "Municipal Solid Waste Landfills, Volume 1:" Summary of the Requirements for the New Source Performance Standards and Emission Guidelines for Municipal Solid Waste Landfills Office of Air Quality, Planning and Standards, Research Triangle Park, N.C. 27711 http://www.epa.gov/ttn/atw/landfill/lf-vol1.pdf (EPA-453R/96-004): February, 1999.

USEPA, 2006, Optical Remote Sensing for Emission Characterization from Non-point Sources, FINAL ORS Protocol, USEPA OTM-10.

USEPA, 2007, "Evaluation of Fugitive Emissions Using Ground-Based Optical Remote Sensing Technology." Cincinnati: February 2007.

Xu, L., Lin X., Amen J., Welding K. and McDermitt D., 2014, Impact of changes in barometric pressure on landfill methane emission. Global Biogeochemical Cycles. 28, doi:10.1002/2013GB004571.

Young A., 1990, "Volumetric changes in landfill gas flux in response to variations in atmospheric pressure." Waste Management & Research 8(5): 379-385.

What is claimed is:

1. A method for estimating fugitive methane emission rate over the surface of a landfill and similar fugitive methane emission surfaces, by sole measurement of surface methane concentration and using a generalizable correlation equation between surface concentration of fugitive methane measured at the surface of different zones of fugitive methane emitting surface, and corresponding emission rates adjusted against barometric pressure, the method comprising:

a. Dividing an area of interest into a plurality of zones ($Z_i$) based on any one or any combination of the following attributes:
   i. The geometry of the site,
   ii. Type of cover,
   iii. Type of vegetation,
   iv. Status of vegetation in terms of density, health and level of stress,
   v. Expected emission levels in form of concentration or rate based on any previous field measurement records,
   vi. Expected emission levels in form of concentration or rate based on the results of previous emission rate or concentration modeling;

b. Sampling of surface methane concentration (SMC) in accordance with any of existing protocols and standards for qualitative assessment of emissions from municipal landfills established by regulatory organizations;

c. Adjusting SMC values ($SMC_a$) to account for effects of barometric pressure rate of change during the sampling;

d. Measuring Methane Emission Rate (MER) in each zone ($Z_i$);

e. Calculating an average $SMC_a$ ($SMC_{a-i}$) for each zone ($Z_i$);

f. Calculating an average MER ($MER_{a-i}$) for each zone ($Z_i$);

g. Correlating the average $SMC_a$ ($SMC_{a-i}$) linearly to the average MER ($MER_{a-i}$) for each zone to obtain a Correlation Factor ($C_f$); and h. Converting SMC measurement data points into MER values for every zone over the entire methane emitting surface using the Correlation Factor ($C_f$);

Wherein for any methane emitting surface a site-specific value for $C_f$ can be calculated using steps a.-g., and the site-specific $C_f$ can then be used to calculate MER from SMC for each specific site.

\* \* \* \* \*